United States Patent [19]

North, Jr.

[11] Patent Number: 5,030,002

[45] Date of Patent: Jul. 9, 1991

[54] METHOD AND APPARATUS FOR SORTING PARTICLES WITH A MOVING CATCHER TUBE

[75] Inventor: Howard L. North, Jr., Los Gatos, Calif.

[73] Assignee: Becton, Dickinson and Company, Franklin Lakes, N.J.

[21] Appl. No.: 392,698

[22] Filed: Aug. 11, 1989

[51] Int. Cl.$^5$ .................... G01N 21/05; G01N 15/02; B07C 5/02

[52] U.S. Cl. ...................................... 356/73; 356/336; 356/337; 209/3.1

[58] Field of Search ........................... 356/39, 73, 341; 250/283; 209/552, 606, 643, 576, 577, 579, 644; 406/1, 3

[56] References Cited

U.S. PATENT DOCUMENTS

| | | | |
|---|---|---|---|
| 4,526,276 | 7/1985 | Schoor et al. | 209/552 |
| 4,756,427 | 7/1988 | Gohde et al. | 209/552 |
| 4,790,653 | 12/1988 | North, Jr. | 356/73 |
| 4,844,610 | 7/1989 | North, Jr. | 356/73 |

Primary Examiner—Vincent P. McGraw
Assistant Examiner—LaCharles P. Keesee
Attorney, Agent, or Firm—Aaron Passman; Nanette S. Thomas

[57] ABSTRACT

A sorter with a body member passageway has analysis, pre-analysis and post analysis portions for particles. An elongate catcher tube carried on the body member, and mounted with its axis to be selectively aligned with the analysis portion for intermittently receiving analyzed particles. An operator receives a signal from the analysis portion relative to one or more particle characteristics and selectively aligns the catcher tube in fluid communication with the analysis portion. The signal is an electrical pulse of strength and timing sufficient to cause a driver mounted to the body member and associated with the catcher tube to align the catcher for sorting particles. A resilient support attaches the catcher tube to the body member and provides a pivot for the catcher tube. A method for sorting includes generating a signal representative of one or more characteristics of the particles and applying the signal to a driver to change the position of the catcher tube.

27 Claims, 5 Drawing Sheets

METHOD AND APPARATUS FOR SORTING PARTICLES WITH A MOVING CATCHER TUBE

BACKGROUND OF THE INVENTION

1. Field of the Invention.

The present invention relates to a catcher tube sorter system for a particle flow through apparatus which includes a catcher tube selectively alignable with the flow from the apparatus, and more particularly, concerns a flow cytometer for determining one or more characteristics of particles flowing through the cytometer with such a catcher tube sorter to provide separation of the particles according to the determined characteristics. The method of sorting with a positionable catcher tube is also a part of the present invention.

2. Background Description.

There are a number of cell or particle analyzing devices using flow cytometer equipment and techniques which rely on hydrodynamically focused fluid flow through an analysis orifice where the specific characteristics of the flowing cells or particles can be determined. Flow analysis of particles has been used in the determination of the variety of characteristics of individual particles. This analysis is most useful in determining characteristics of cells for the collection of information which would aid in areas of research, hematology, immunology and the like. The researcher, for example, could be interested in determining specific characteristics of the individual cells where those cells need to be classified, identified, quantified and preferably sorted for further investigations or analysis.

One commercially available flow cytometer which relies on a hydrodynamically focused fluid system is known as the FACScan ™ instrument sold by Becton Dickinson Immunocytometry Systems, San Jose, Calif. The FACScan ™ instrument rapidly analyzes cells on the basis of fluorescence and light scatter properties. Analysis is accomplished by introducing cells in suspension to the center of a focused liquid stream thus causing them to pass, one at a time, through a focused light from a high power laser. Each cell is individually characterized by its light scatter signals and by the intensity and color of fluorescence emitted while it is illuminated.

In the aforementioned flow cytometer, a sheath liquid focuses the particles or cells as they pass through the orifice associated with the analyzing or counting capabilities. U.S. Pat. Nos. 4,503,385 and 4,526,276 describe particle analysis systems in which particles flowing in a stream are enveloped in a sheath liquid which focuses and confines the sample liquid (with the particles or cells) to the center of the flowing stream. U.S. Pat. No. 4,110,604 describes a particle density measuring system in which particles flowing in a stream are enveloped in a sheath liquid which focuses and confines the sample fluid (with the particles) to the center of the flowing stream.

In the presently known and available flow through equipment, electrically operated pumps, syringe pumps or the like are used in the fluidics of the system to move the liquid and particle flow through the flowcell analysis orifice and passageways. The usual operation for these pumps is to force or draw liquid with particles from a sample test tube through a sample capillary uptake tube centered in the sheathing liquid flowing in the direction of the particle analysis orifice. The Assignee of the present application has a U.S. Pat. No. 4,790,653, issued Dec. 12, 1988, disclosing a housing for a flow cytometer with a particle unclogging feature; and copending applications, U.S. Ser. No. 125,095 filed Nov. 25, 1987 disclosing a sheathed particle flow controlled by differential pressure and U.S. Ser. No. 188,582 filed Apr. 29, 1988 disclosing a backflow isolator and capture system. All of these inventions are useful with the present invention.

"Electronic Separation of Biological Cells by Volume" by M. J. Fulwyler in Science vol. 150, pp. 910–911, November (1965) or "High-Speed Cell Analysis and Sorting with Flow Systems: Biological Applications and New Approaches" in IEEE Trans. on Nuclear Science, NS-21, pp 714–720 (1973) describe devices where the suspension stream is charged by suitable equipment shortly before the break-off of the droplet containing the particle after detecting the desired characteristic within an optic electronic system. A very strong electrostatic field of several thousand volts per centimeter, breaks up the flow of particle containing droplets into two or more streams depending on the polarity and charge of the droplets, and the various divided streams are collected in different small containers. Particle sorters of the type relying upon electrostatic separation of particles are described in U.S. Pat. Nos. 3,380,584; 3,710,933; 3,826,364; 4,148,718; 4,230,558; and 4,138,480.

The particle sorters which rely upon an electrostatic field for separating and sorting particles have particles charged with the same electrical polarity accumulate in respective collection wells. The result is that the collection well itself assumes the electrical polarity of the particles being collected. Once this electrical charge of the collection well is established, incoming particles of the same polarity are deflected because of the electrostatic force operating to separate charges of like nature. Removing the charge by a ground wire in the collection vessel is known. These sorters may produce aerosols which must be contained to avoid biological hazards to nearby personnel when sorting pathogenic particles.

U.S. Pat. No. 4,175,662 includes a method and apparatus for sorting of particles or cells in accordance with their physical or chemical properties where sorting is achieved after the particles are analyzed by reliance upon an electrolysis gas pressure impulse which causes a deflection of the particle suspension stream and flow into a different channel. This sorter may cause disturbances to the particle flow thru the laser beam thus interfering with the optical analysis of the particles.

An easily adapted sorter which does not rely on the deflection of the particles is required in order to minimize movement of, eliminate contact with, and prevent damage to the particles. With the foregoing in mind, improved techniques for sorting particles in a flow cytometer sample are still being sought. Such improvements in the simplification of sorting hardware and the adaptation and application of such hardware to a flow cytometer or other particle analyzer are needed. An improvement related to avoidance of biologically hazardous aerosols and to avoidance of pressure pulses which can disturb the optical alignment of the analysis apparatus is needed. It is toward such an improvement that the present invention is directed.

SUMMARY OF THE INVENTION

A preferred form of the present invention includes a catcher tube sorter for a flow cytometer with a body member and passageway for particles to be analyzed.

The passageway has an analysis portion, a pre-analysis portion and a post analysis portion. An uptake tube is connected in fluid communication with the pre-analysis portion and adapted for fluid communication with a source of particles containing samples of particles for providing a flow path from the source of particles into the flow cytometer analysis portion.

A catcher tube is carried on the body member and is mounted so it may be selectively positionable in fluid communication with the analysis portion for intermittently receiving analyzed particles after passage of the particles through the flow cytometer analysis portion. An operator receives an input signal from the analysis portion relative to one or more particle characteristics and then moves the catcher tube into fluid communication with the flow cytometer analysis portion.

A sheathing liquid is introduced into the pre-analysis portion about the uptake tube inner end to provide a sheathed flow of particles along an axis of the passageway toward the analysis portion. In one preferred form the flow cytometer may have a flowcell having an orifice sized to permit the passage of substantially one particle at a time through the analysis portion such that the input signal is an optical response to one or more particle characteristics. The post analysis portion is arranged about the catcher tube to receive and draw away particle flow not selectively caught in the catcher tube. In the preferred form the input signal is a pulse of strength and duration sufficient to selectively position the catcher tube in fluid communication with the analysis portion. A driver mounted to the body member and associated with the catcher tube receives the input signal pulse and selectively positions the catcher tube in at least partial alignment for fluid communication with the analysis portion. The catcher tube has an axis and is carried on the body member for movement of its axis into at least partial alignment with the analysis portion.

In another form of the preferred embodiment a catcher tube sorter for a particle flow through apparatus comprises a body member having a passageway therethrough including an analysis region through which substantially one particle at a time may pass in the direction of flow when the apparatus is operating. A supply of particles connected in fluid communication with the passageway provide the analysis region with substantially one particle at a time. A sheathing liquid is applied to the supply of particles in the passageway for hydrodynamically focusing the particles relative to the liquid.

A catcher tube means is preferably supported upon the body member for fluid communication with particles from the analysis region. For culling particles from the analysis region, the catcher tube means is positionable to a position substantially in alignment with the particle flow from the analysis region from a position where the catcher tube means is aligned with the particle-free flow from the analysis region. A control means operatively responds to particles of one or more preselected types passing through the analysis region. The control means may be arranged for moving the catcher tube between the positions substantially into and out of alignment with the particle flow.

The catcher tube means may include a resilient support which is stressed upon movement of the catcher tube means between positions. Similarly, the control means is responsive to at least one characteristic of one or more particles passing through the analysis region for activating a driver in the control means thereby flexing the resilient support.

In yet another arrangement in a flow cytometer with a body member passageway for particles analysis, the passageway has an analysis portion, a pre-analysis portion and post-analysis portion disposed along an axis. An uptake tube has an inner end positioned in the pre-analysis portion of the passageway near the analysis portion and an outer end extending outwardly of the body member and inserted into a sample supply containing liquid and particles. The uptake tube has a lumen extending therethrough for the passage of the particles toward the analysis portion. A flowcell with an orifice sized to permit the passage of substantially one particle at a time is included in the analysis portion. In the post analysis portion there is a catcher tube sorter mounted for selective alignment with an exit from the flow cell.

In the preferred device a catcher tube is moved, in response to regulating means, into fluid communication with the analysis portion by substantially aligning the catcher tube and an axis through the analysis portion. The catcher tube is preferably elongated relative to its axis and a flexible support attaches the catcher tube to the body member for carrying the catcher tube in a position for realignment of the catcher tube axis with the passageway axis so that the axes are substantially parallel to one another.

The elongate catcher tube includes a pair of ends and a central section therebetween and the flexible support is mounted between the central section of the catcher tube and the body member thus permitting pivotal movement of the catcher tube about a point along the axis of the catcher tube. The catcher tube swings into an axial alignment substantially parallel with the particles passing one at a time in a stream, from the flow cell and in alignment with the passageway axis so that the axes are coaxially in line with one another. The catcher tube has a driver located between one end of the catcher tube and the body member for moving the opposite end into coaxial alignment with the particle stream.

A method for sorting particles passing through a particle analysis apparatus is another form of the invention wherein a sample of particles carried in a liquid is transported by air pressure applied to the liquid. The method includes generating a signal representative of one or more characteristics of the particles passing through an analysis region of the analysis apparatus and applying the signal to a driver for changing the position of a catcher tube so that the catcher tube is moved to receive the particles having one or more characteristics.

The step of applying the signal to the driver for changing the position of the catcher tube may include flexing a support for the catcher tube to bring the catcher tube into substantial alignment with the particles passing through the particle analysis apparatus and which particles have one or more of the characteristics sought to be sorted. The step of generating a signal representative of one or more characteristics of the particles passing through an analysis region may include using light to analyze the particles passing one at a time through the analysis region to provide an electrical signal. The step of using light to analyze the particles passing one at a time through the analysis region to provide a signal may include the step of applying the signal to a driver for changing the position of the catcher tube. The step of flexing a support for the catcher tube to align the catcher tube with the particles may include pivoting the catcher tube about a point.

BRIEF DESCRIPTION OF THE DRAWINGS

FIG. 2 is a schematic illustration of a preferred embodiment of the optical elements and light paths of a flow cytometry apparatus of the present invention for determining one or more characteristics of cells of the like;

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 1:
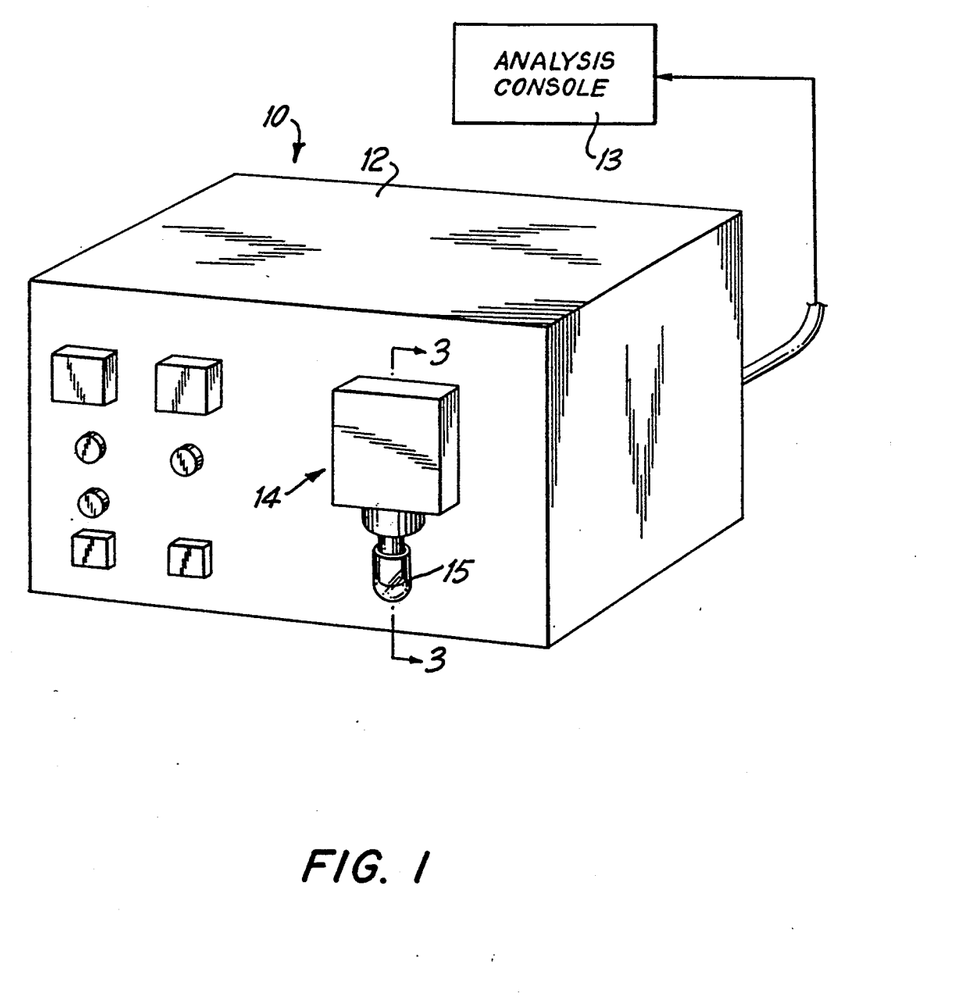
FIG. 1 is a perspective view of the preferred embodiment of a flow cytometer analyzer including a catcher tube sorter for use in determining one or more characteristics of particles or the like flowing in a liquid stream.

Referring to the drawings, and FIG. 1 in particular, there is illustrated a flow cytometry apparatus 10 of the present invention for determining one or more characteristics of particles or the like. Apparatus 10, for example, may be a cell analyzer which includes a liquid sampling console 12 which is constructed to contain particle or cell detection and analysis elements as hereinafter described. In particular, apparatus 10 includes a liquid sampling console 12 which is constructed to contain the particle, light scatter and fluorescence measuring components, as hereinafter described, but which is separate from the analysis console 13. Analysis console 13 includes the electrical components, display screens and other data information regarding the control and function of the apparatus 10. Liquid sampling console 12, as seen in FIG. 1, includes a flow manifold assembly in the form of a housing 14 which is designed to provide a stream of flowing liquid containing the particle to be analyzed. In the apparatus being described, the particles for analysis may be included in a source of particles or test tube 15 which may be sealably engaged onto housing 14. Before describing the details of housing 14, a general description of the optical and flow elements of flow cytometry apparatus 10 will be provided.

Figure 2:
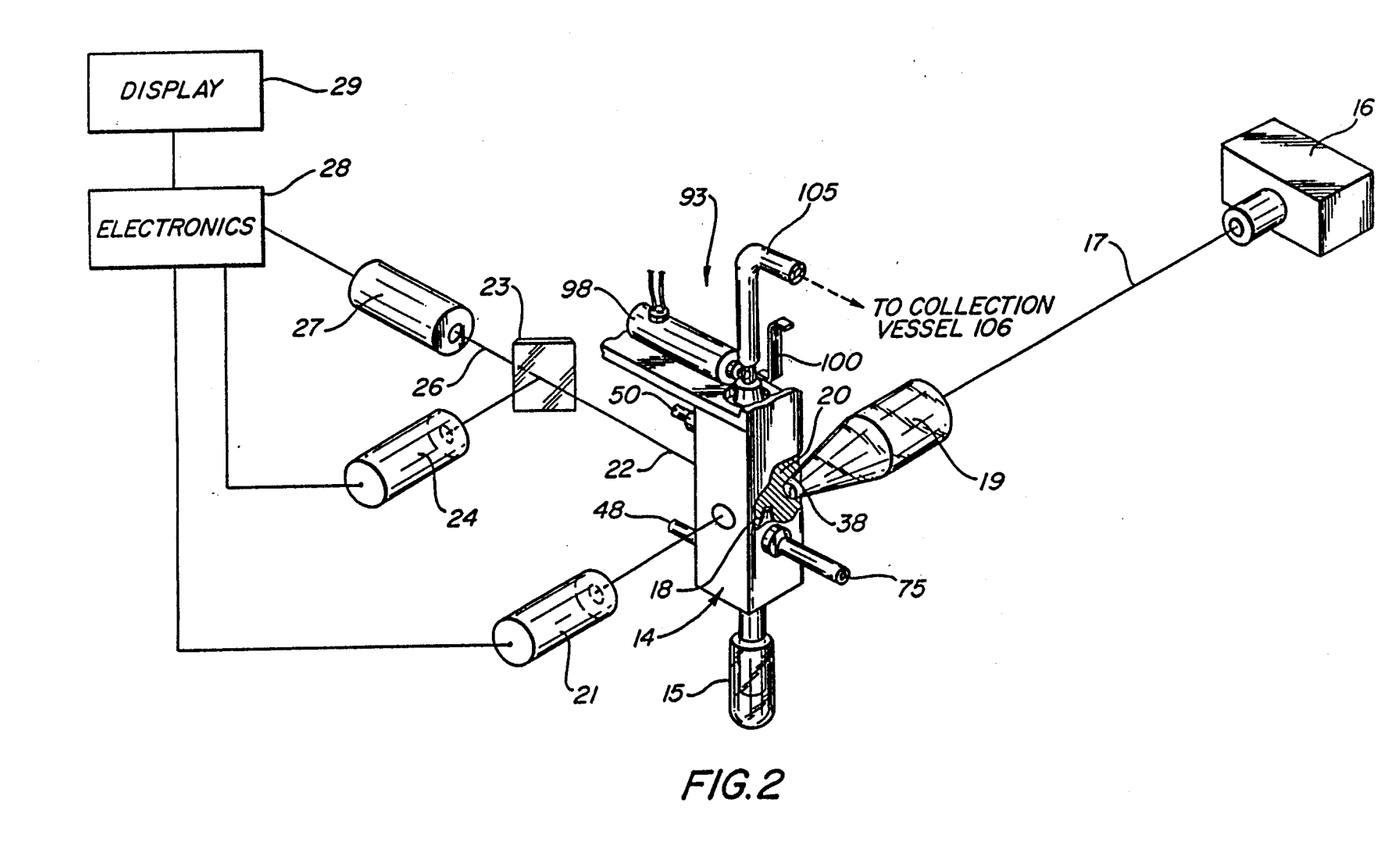

In the drawings, and FIG. 2 in particular, the optical and particle flow elements of a flow cytometry apparatus 10 are illustrated. The optical and flow elements of FIG. 2 represent the major components of the flow cytometry apparatus 10 for moving particles, such as cells or the like, in a liquid stream, substantially one at a time, in order to assess those particles for specific characteristics thereof. For example, the elements of the device of FIG. 2 may be included in a FACScan analyzer, manufactured and sold by Becton Dickinson Immunocytometry Systems, San Jose, Calif. for cytometric study on the basis of light scatter and fluoresence in a wide variety of research laboratory applications. The optical and flow elements to be described in more particular detail may be embodied in the FACScan analyzer. It is understood that the present invention is useful in many different types of flow fluorometric or flow cytometry apparatuses, whether measuring light scatter, particle volume, fluorescence or other optical parameters for the identification or quantification of cells or the like in a sample liquid medium.

As illustrated in FIG. 2, light entry is provided for the present flow cytometry apparatus 10 by a light source 16 such as a laser which provides a linearly polarized collimated beam 17 of light at a singular wavelength or at a number of discreet wavelengths. Alternatively, light source 16 may be broad-spectrum arc lamp, such as mercury or xenon, with polarizing means included in excitation light path 18 produced by light source 16. Typically, apparatus 10 also includes a lens 19 which focuses the light beam 17 at a liquid stream 20 containing the particles or cells under investigation.

A nozzle, incorporated within the flow cytometry apparatus 10 of the present invention, facilitates the flowing of cells or particles within liquid stream 20. The use of a nozzle is well-known and is described, for example, in U.S. Pat. No. 3,826,364. The nozzle provides a hydrodynamically focused flow of cells in the liquid stream 20 comprising a sheath fluid and particles or cells 68 in FIG. 3. As each cell or particle passes through where the focused light beam 17 intersects liquid stream 20, light scattered thereby may be detected.

As each cell or particle passes through the focused light region where light beam 17 intersects the flowing liquid stream, light scattered by the cell or particle can be detected by an appropriate silicon photodiode 21. Similarly, fluorescence, if emitted by particles energized by the illumination from the light source, can also be detected. Fluorescence emitted by autofluorescent particles or fluorescently labeled or stained particles in the liquid stream 20 can be detected.

Photodetector 21, as illustrated in FIG. 2, is positioned to receive light scattered forwardly by each cell. Fluorescence, if emitted by cells energized by the illumination from the light source 16, may also be detected. Similarly, light scattered in different directions, besides the forward direction, may be detected. In laser excited flow cytometry, both fluorescence and wide angle light scatter are typically collected at an angle whose viewing axis is 90° relative to the excitation axis of light beam 17. In FIG. 2, axis 22 represents the 90° viewing access for the collection of fluorescence and wide angle scatter. Thus, light traveling along axis 22 includes both light scatter and fluorescence as its components.

In order to collect fluorescence and light scatter at the 90° angle from the incident laser beam 17 the light scatter and fluorescence should be separated or split. To accomplish such splitting dichroic filters or a beam splitter 23 is used to receive both scattered light and fluorescence at the 90° angle and to re-direct each such component in different directions. Such re direction of light scatter and fluorescence then permits the light scatter and fluorescence to be collected separately, even though both originate at the 90° angle.

For example, the reflected light scatter may be detected by a photomultiplier tube 24. If the fluorescence includes a number of different color regions, a dichroic mirror 23 may be used to separate the different color wavelengths. Thus, and for example, fluorescence in the green color region may be transmitted by dichroic mirror 23 along axis 26 and collected in an appropriate photodetector 27. Additional dichroic mirrors may be included as in U.S. Pat. No. 4,662,742 for associating the fluorescence colors with additional characteristics of cells or particles analyzed. In FIG. 2, those skilled in the art will appreciate that various lenses, filters, barriers or the like may be employed in conjunction with each additional photodetector to obtain as pure a signal as possible. Obtaining such optically clean signals is most desirable particularly when fluorescence and light scatter channels are used, as in the apparatus illustrated in FIG. 2.

The electrical signals from photodetectors 21, 24, and 27 are typically fed as discrete pulses to the electronics 28 of the apparatus for purposes of display 29, storage or further processing so that one or more characteristics of the cells or particles under analysis can be determined or sorted as will be described in detail herein. Electronics 28 may be included in an analysis console 13, if desired.

Figure 3:
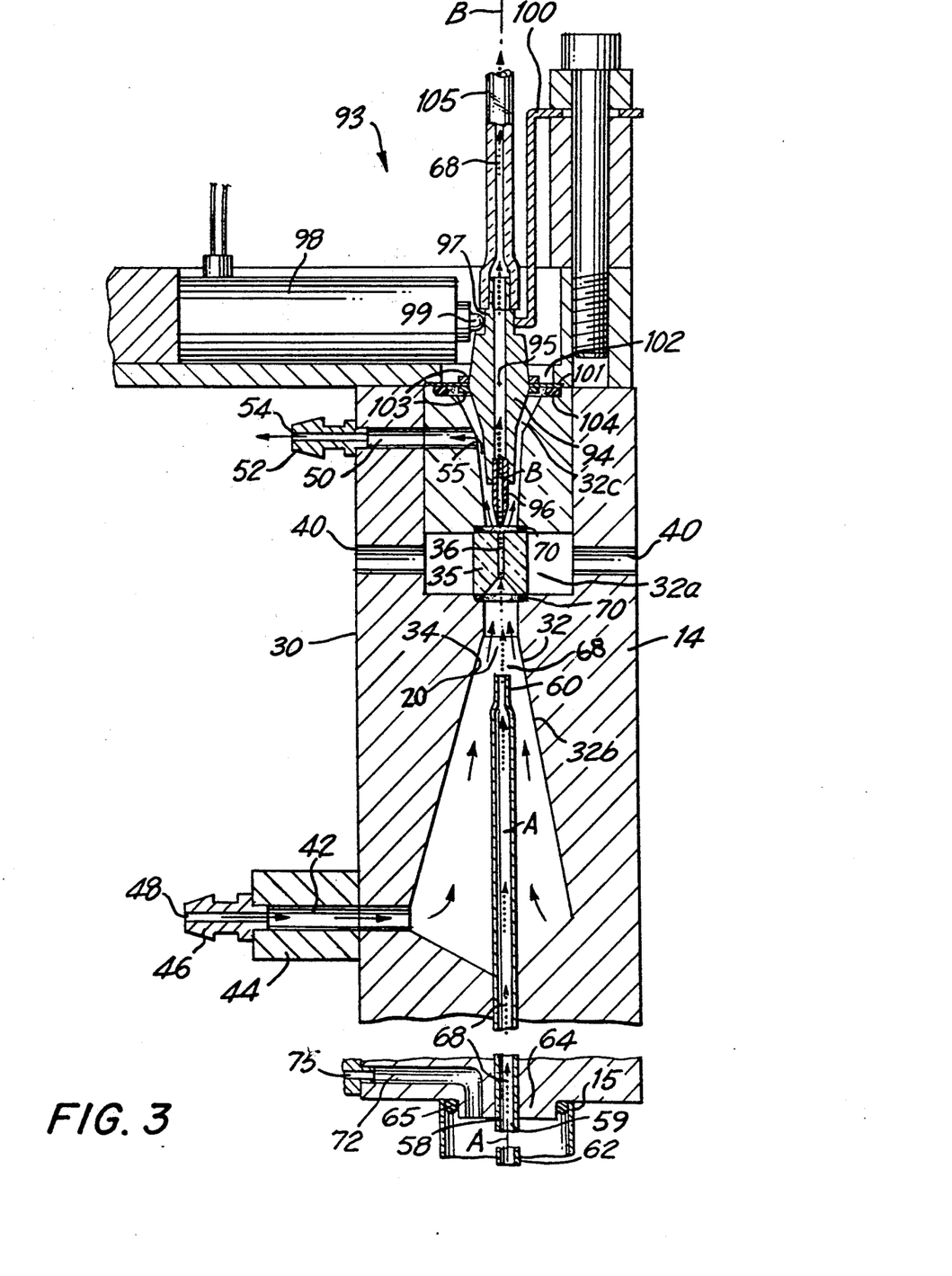
FIG. 3 is an enlarged cross-sectional view of the preferred flow housing and catcher tube sorter of the present invention taken along line 3—3 of FIG. 1.

Turning now to FIG. 3, the details of housing 14 of the present invention are more clearly illustrated. It can be seen that housing 14 includes a body member 30 which, in the embodiment being described, is preferably in the form of a block or rectangular prism. Although not shown in the drawings, the block form of housing 14 facilitates the mounting of the housing within the flow cytometer apparatus 10. Extending through housing 14 is a passageway 32 which is defined by three regions: an analysis portion 31a, a pre-analysis portion 32b, and a post analysis portion 32c. As seen in FIG. 3, the pre-analysis, analysis and post-analysis portions of passageway 32 lie on an axis A through body member 30 and are arranged in that order relative to the direction of particle flow indicated by arrows through the passageway 32.

It is preferred that pre-analysis portion 32b and post analysis portion 32c of the passageway be axisymmetrical shaped bores extending into body member 30. It is preferred that pre-analysis portion 32b of the passageway be tapered so that it includes tapered walls 34 defining a frustoconical passageway having its narrow end facing toward analysis portion 32a of the passageway.

Preferably positioned within analysis portion 32a of the passageway is a flowcell or flow chamber 35 which facilitates the analysis of cells or particles under investigation. Flowcell 35 includes an orifice 36 which is preferably rectangular in cross section and sized to permit the passage of substantially one particle at a time therethrough. As a light beam intersects the region defined by orifice 36, particles pass through the light beam thereby establishing a basis for a light-related signal which can be detected.

So that light energy can be available to illuminate the region defined by orifice 36 in the flowcell, body member 30 of the housing includes a recess 38, as shown in FIG. 2, into which lens assembly 19 is positioned so that the lens assembly lies adjacent flowcell 35. This type of arrangement suggested by the illustration in FIG. 2 is consistent with a technique for providing light energy to interrogate the particles under analysis. Light is directed through lens assembly 19 at an angle substantially orthogonal or at a right angle to the aforementioned direction of particle flow through the flowcell. Lens assembly 19 can include one or more lenses in a condenser lens assembly for focusing incident light on the particles which pass through orifice 36 and may receive light such as fluorescence from the particles which have been illuminated by the incident light beam 18. Of course, the present invention contemplates that light from the particles may be detected in any direction with respect to the axis of the incident light beam.

The appropriate light detectors are positioned at the desired angle for collecting light scattered or emitted by the particles or for detecting light energy absorbed by the particles. To this end, as seen in FIG. 3, one or more windows 40 extend through body member 30 into flowcell 35 through which light passes for collection by the photodetector elements. On the other hand, it is not necessary to provide such a window if body member 30 is sufficiently light transmissive to allow light to pass therethrough in sufficient strength to be detected. It is, however, preferred that flowcell 35 be light transmissive and also that the flowcell be removable from body member 30 in the event that it needs cleaning, replacement or change.

Body member 30 also includes a first channel 42 which is in fluid communication with pre-analysis portion 32b of the passageway. Channel 42, in this embodiment, extends through a side block 44 of body member 30 so that this channel is substantially at right angles to the axis A of passageway 32. Side block 44 connects with an enlarging conduit which reduces fluid velocity entering the pre-analysis portion 32b and thus reduces the flow disturbances associated with the change in direction of the fluid flow. A fluid connector 46 is positioned on side block 44 so that its lumen 48 is in fluid communication with channel 42. It is the purpose of channel 42 to provide a passageway for the introduction of a liquid for sheathing particles which flow into analysis portion 32a of the passageway, and which more specifically flow through flowcell 35.

The provision of a sheath liquid for a hydrodynamically focused fluid flow system is well known and is described in the mentioned patents. The sheath liquid is generally pressurized with air and typically flows through channel 42 at a pressure of between 0.5 and 10 psi and at a rate of 10 to 20 ml. per minute. The sheath liquid is usually a saline solution which is substantially particle free so that it does not interfere with the analysis.

Communicating with post-analysis portion 32c of the passageway is another channel 50 which also extends through body member 30 in the embodiment being described. Channel 50 preferably extends at substantially right angles to the axis of passageway 32. In fluid communication with channel 50 is a fluid connector 52 having a lumen 54 therethrough. It is the purpose of channel 50 to provide one exit for the passage of particles and liquids out of housing 14 after passing through the analysis portion of the passageway. It can be seen that channel 50 has its interior end 55 preferably open to post analysis portion 32c of the passageway.

Particles or cells to be analyzed are preferably transported through a hollow uptake tube 58 with a lumen 59 extending therethrough. Uptake tube 58 extends substantially along the axis A of passageway 32 and has an inner end 60 positioned in pre-analysis portion 32b of the passageway. It is preferred that inner end 60 be positioned within tapered walls 34 of the pre-analysis portion so that the inner end 60 of the uptake tube lies in a region at low fluid velocity in the pre-analysis portion 32b of the passageway. Uptake tube 58 has its outer end 62 extending outwardly of body member 30. The body member of the housing preferably includes a circularly shaped extension 64 through which tube 58 extends before passing outwardly of the body member. A seal member 65, or other like element for providing a gas-tight seal, is positioned around circularly shaped extension 64. It can be seen in FIGS. 3 and 4 that test tube 15 is positioned so that it fits onto extension 64 with seal member 65 facilitating a gas-tight seal between the test tube and extension 64 of the body member. Test tube 15 includes sampling liquid 66 and particles 68 to be analyzed. Outer end 62 of the tube extends into sampling liquid 66.

In order to seal flowcell 35 within body member 30 there are a pair of ring gaskets 70 in the form of O-rings received within recesses in the body member 30.

A channel 72 extends through body member 30 and is in fluid communication with the interior of test tube 15. A lumen 75 is in fluid communication with a source of regulated pressurized air or other fluid to serve as a driving force of pressure into the test tube 15 so that sampling liquid 66 and particles 68 may pass through lumen 59 of uptake tube 58. Normally, the air is delivered through lumen 75 at a slightly higher pressure than that applied to drive the sheath liquid through channel 42. In the preferred case, the regulated air pressure may be controlled at 5.0 psi or 4.0 psi for a selected high or low flow rate of 1.0 microliters per second, or 0.20 microliters per second, respectively.

Particles 68 pass out of the inner end of the tube into pre-analysis portion 32b of the passageway. Here, the particles and sampling liquid become ensheathed by the sheathing liquid so that the particles pass substantially one at a time through orifice 36 in flowcell 35, as seen in FIG. 3. The confluence between the sampling liquid (and particles) and the sheath liquid form a coaxial, bi-component stream. The sampling liquid containing the particles 68 to be analyzed forms the inner component of the flowing stream. When the stream enters the flowcell 35, there is substantial equilibration in the velocities of the sheath liquid and the sample liquid and the particles are hydrodynamically focused or centered in the middle of the stream away from the walls of the flowcell 36.

Once in the flowcell, the particles are interrogated by light which enters the flowcell through lens assembly 19 so that light-related information may be determined with respect to each particle. After the particles, sampling liquid and sheathing liquid pass through the analysis region of the passageway, flow continues into the post analysis portion 32c of housing 14.

It is appreciated that the various air pressures and resulting flow rates could be manually adjusted by controls on the liquid sampling console. A typical sample flow rate is in the range of 0.2 to 1.0 microliters per second of sampling liquid through the sampling tube. Furthermore, the air pressure in lumen 75 may be adjusted to control the analysis rate of particles through the flow chamber. Typically, the analysis rate would range between 10 and 1,000 particles per second flowing through the flow cell 35. The design of passageway 32 and the positioning of uptake tube 58 therein is intended to offer minimal flow resistance and turbulence to the bi-component stream of liquid as it flows toward flowcell 35.

Figure 4:
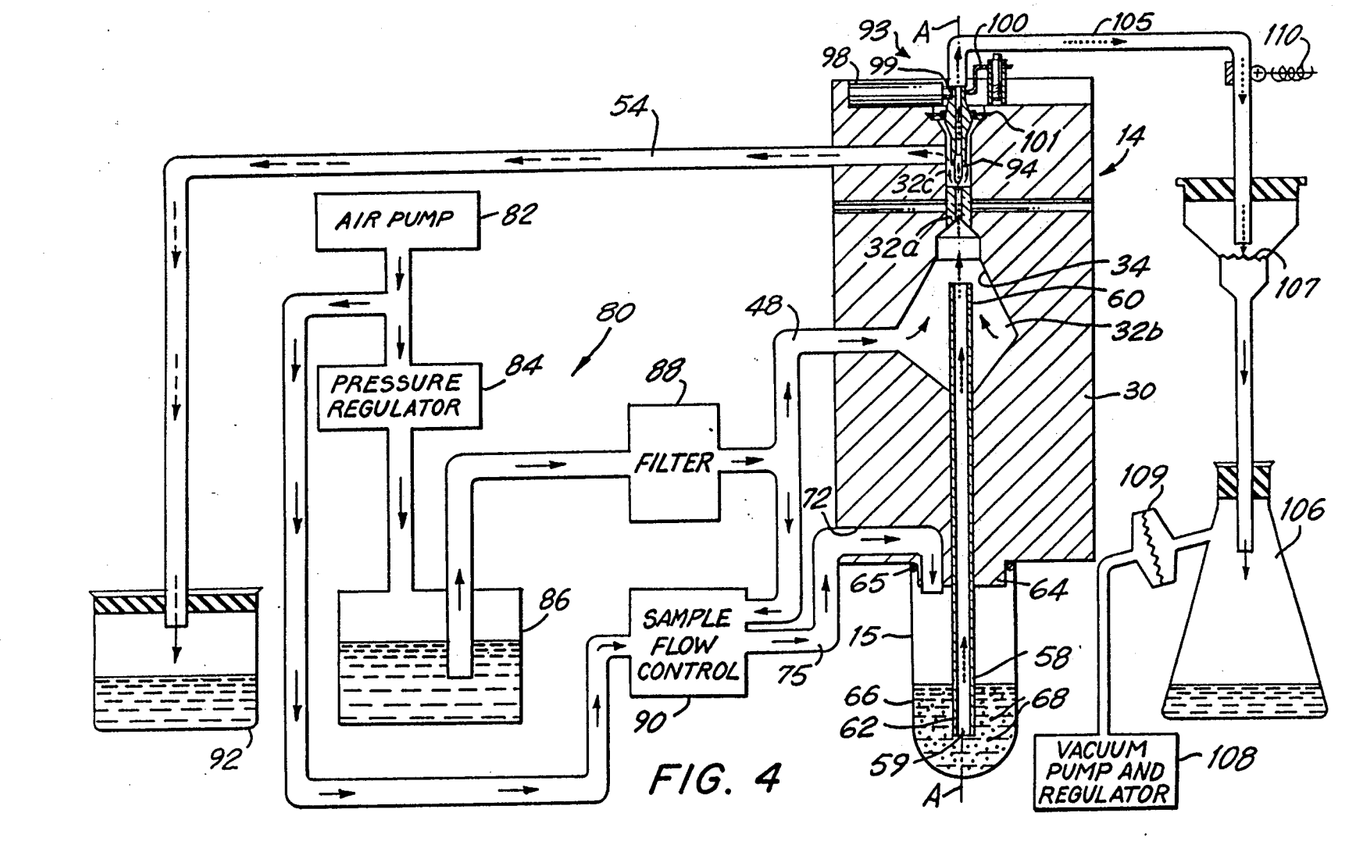
FIG. 4 is a schematic illustration of the relationship of the catcher tube sorter operative elements and the flow paths between the element including the connections of the control with the analyzer of FIG. 1.

In FIG. 4 there is a schematic illustration of the control 80 whereby the flow rate of particles 68 is regulated. The control 80 includes an air pump 82 connected to a pressure regulator 84 adjusted to provide a head pressure input of about 4.0 psi to the sheath liquid supply reservoir 86. The outlet from reservoir 86 is preferably connected to a filter 88 which removes any particulate matter from the sheath liquid as it is transported to the lumen 48 of housing 14.

Air pump 82, in FIG. 4, is also connected to the sample flow control 90 for regulating pressurized air to be used to drive the liquid 66 and particles 68 through uptake tube 58 into pre-analysis portion 32b of housing 14. In the preferred arrangement sample flow control 90 regulates the air pressure applied to test tube 15 through lumen 75 so that the pressure is at 4 psi or 5 psi depending upon whether a low or a high flow rate of particles 68 is desired. A waste reservoir 92 as part of post-analysis portion 32c is connected to lumen 54 to collect a part of the liquids and particles after they have passed through the passageway 32. The sorted particles are caught as will be explained.

In FIG. 3 the details of the catcher tube sorter 93 are shown. The schematic diagram of FIG. 4 best illustrates the overall system. In particular, the test tube 15 has the driving air pressure supplied through lumen 75 to move particles through lumen 59 of the uptake tube 58. In the post analysis portion 32c just after the analysis portion 32a is an elongated catcher tube 94. Catcher tube 94 is positioned to be movable into substantial alignment with the axis A passing upwardly through the uptake tube 58 and through the orifice 36. The catcher tube 94 is a capillary tube with a tapered ceramic tip and is movable for substantially parallel and nearly coaxial alignment with the axis A. In particular, and as best shown in FIGS. 3 and 6, an axis B of the catcher tube 94 is pivotal about a point 95 located between a lower end 96 of the catcher tube 94 and an upper end 97 of the catcher tube 94.

The catcher tube 94 is a two piece construction. The lower end 96 is preferably made of alumina ceramic by Small Precision Tools of Petuluma, Calif. as a nailhead capillary bonding tip model NS-60 with a 150 micron inside diameter at the tip. The upper end 97 is a stainless steel support.

Figure 5:
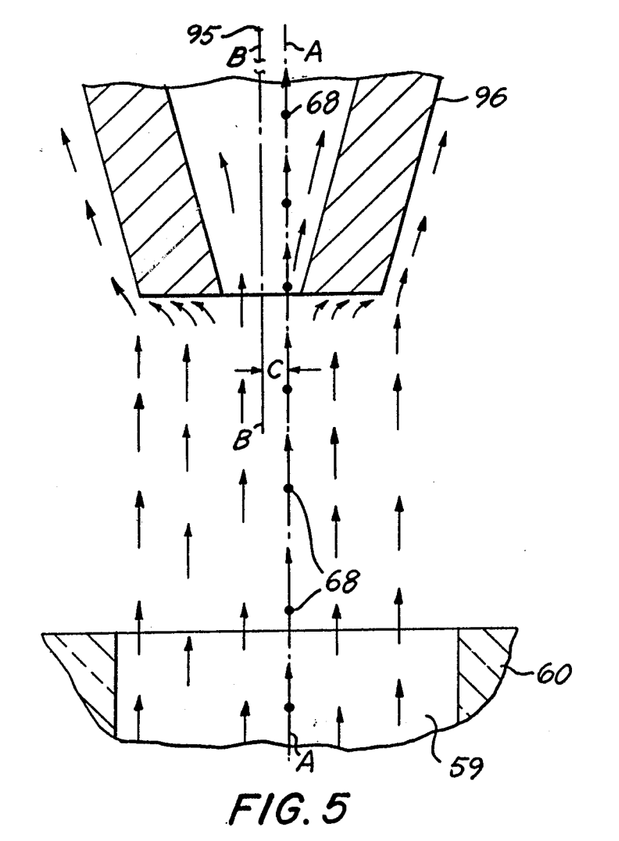
FIG. 5 is an enlarged schematic illustration of the catcher tube showing sorting of particles as performed when the catcher tube is in the aligned position.

As shown in FIG. 5 the catcher tube 94 pivots into substantial coaxial alignment with the axis A when driven by the driver 98 shown in FIGS. 3 and 4, but the catcher tube axis B is only nearly coaxial with axis A, being spaced a small distance C from the axis A when pivoted by the driver 98 to the position shown in FIG. 5. The 150 micron inside diameter at the inlet, entry, tip or lower end 96 of the catcher tube 94 cooperates with the rectangular orifice of the flowcell 36 which is 180 by 430 microns. The width of the orifice of the flowcell 36 is 430 micron. A larger inside diameter would allow the catcher tube to pick up fluid accumulating at the orifice exit containing some of the particles 68. A smaller inside diameter would promote more frequent clogging of the inlet, entry, tip or lower end 96 of the catcher tube 94. Thus the inside diameter of the catcher tube 94 should be equal to or slightly smaller than the minimum dimension across the orifice of the flowcell 36. Obviously if the recirculating fluid at the exit of orifice 36 were replaced by a particle free fluid the inside diameter of the catcher tube 94 could be larger than the minimum dimension at orifice 36.

Figure 6:
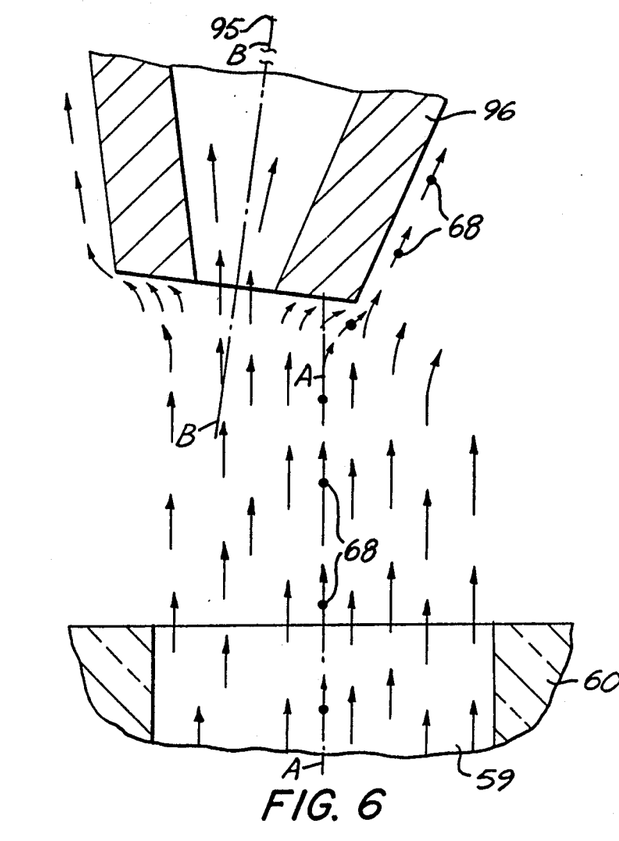
FIG. 6 is an enlarged schematic illustration of the catcher tube showing that particle sorting is not performed when the catcher tube is in the displaced or unaligned position when particle sorting is not required.

The rectangular shape of the flowcell 36 orifice allows the catcher tube 94 to be positioned off or displaced from the particle stream as illustrated in FIG. 6 and still be fully in the sheath fluid exiting the orifice of the flow cell 36. This avoids fluid recirculating at the orifice exit from entering the catcher tube 94 and contaminating the collection conduit and filter with particles present in the recirculating fluid.

The driver 98 is mounted upon body member 30 and is located such that a bearing 99 on the driver 98 contacts the catcher tube 94 near the upper end 97 for positioning of the catcher tube 94. In the preferred embodiment the bearing 99 is a spherical shape that provides point contact with the catcher tube 94 upper end 97. The point contact is such that the force of the driver 98 is applied to the upper end 97 substantially normal to the axis B causing the pivotal motion of the catcher tube 94 about the point 95. The driver 98 is in the preferred embodiment a piezo electric device, such as model P-810.20 PZT translator of the Physik Instrumente (PI) GmbH & Co., which responds to an electrical pulse of 100 volts of sufficient strength and duration to produce an extension in length of 30 microns such that the bearing 99 moves relative to the driver 98 and pivots the catcher tube 94 into substantial alignment with axis A. The circuitry for the driver 98 controls the maximum values of applied voltage and current as well as their time rate of change producing desired position, velocity, acceleration and damping for the sorting, fluidics, and characteristics of the driver 98. The preferred driver 98 has a rated stiffness of 6 N/micron with a resonance frequency of 15 KHz and an electrical capacitance of 0.8 microfarad. The catcher tube 94 is designed to have a low mass and a high stiffness to achieve a high resonance frequency. In the preferred embodiment the catcher tube 94 has a resonance frequency of about 20 KHZ. The driver 98 and catcher tube 94 as a combined mass have a resonance frequency of about 7 KHZ.

The pulse used to activate driver 98 is obtained after the analysis of the particles 68 as with the detector 24 which is described herein in connection with FIGS. 1, 2 and 3. Suitable amplification or modification of the activating pulse is within the skill of practitioners and is therefore not set forth in detail. The preferred translator can be driven at a peak rate of about 1000 times/second by charging and discharging it like a capacitor. A leaf spring 100 is mounted on body member 30 across from bearing 99 and urges the upper end 97 of the catcher tube 94 against the bearing 99. Wires are shown extending from driver 98 for electrical connection in circuit with electronics 28 for the described operation.

A time delay of about 600 microseconds is provided to allow for the particle 68 to travel from where it is detected by the laser to the catcher tube 94 prior to energization of the driver 98. This time delay provides for transit time of the particle 68. In the preferred sorter 93 driver 98 is energized at about 500 microseconds and de energized at about 700 microseconds after a desired particle has passed thru the laser beam and been detected. The electronics 28 can be used to vary the time delay automatically to compensate for variations in particle stream velocity due to changes in fluid temperature, pressure on the supply tank 26 or back pressure in the post analysis portion. This may be done by measuring the transit time of the particle 68 through the laser beam and using that time to set the delay time.

Point 95 may be placed anywhere between the ends 96 and 97 but location of the point 95 closer to bearing 99 is preferred to amplify the 30 micron motion of the driver 98 to obtain in excess of 100 microns of motion at catcher tube end 96 as shown in the FIGS. 3, 4, 5 and 6. A resilient support 101 in the form of a flexible thin metallic diaphragm spans the space between the body member 30 and the catcher tube 94 at the level of point 95 and permits the described pivotal movement of the axis B. The preferred resilient flanged support 101 is made of a spring material such as beryllium copper or the like and is about 0.25 mm. thick whereby flexure about point 95 causes moderate stress in the resilient support 101 and requires very little force from driver 98. The flexure is about 0.005 radian angular excursion producing a bending stress of about 70,000 psi in the diaphragm of resilient support 101. The inertia of the system is therefore minimal and the resonant frequency is high permitting rapid movement of the catcher tube 94 so it is positionable to capture and thereby selectively sort, as will be explained, the desired particles from those particles 68 which have passed through the analysis orifice 36.

In FIG. 3 the preferred configuration of the resilient support 101 is shown partially in section. A pair of upstanding flanges 102 provide the mounting of the resilient support 101 to the body member 30; only one of the upstanding flanges appears in the partial sectional view of FIG. 3. Since the catcher tube 94 upper end 97 to which the the resilient support 101 is connected is stainless steel attaching the beryllium copper of the resilient support is best performed by a pair of press fit metal rings 103. The rings 103 are placed around the central section of the catcher tube 94 with the resilient support 101 captured as in a sandwich between the rings 103. The lower end 96 of the catcher tube 94 is preferably tapered so that the function of the catcher tube 94 when aligned as described will cleanly separate the particles 68 during sorting.

Specifically, the positioning of the lower end 96 within the post analysis portion 32c of the passageway 32 provides an excellent location for selectively intercepting particles of interest. Since the resilient support 101 closes and seals the passageway 32 in the space about the catcher tube 94 by means of an O-ring 104 between body member 30 and the resilient support 101, the exit for the particle flow from the post analysis portion 32c, when the catcher tube 94 is not axially aligned, is through the channel 54 to the reservoir 92.

In FIGS. 5 and 6 two positions of the catcher tube 94 are schematically shown. When pivoted by the driver 98 to be substantially coaxial with axis A, as shown in FIG. 5 the axes A and B are not in exact coaxial alignment but are spaced apart the distance C. It is obvious that some deviation from perfect alignment of axes A and B will still permit the catcher tube lower end 96 to collect desired particles from the particle stream essentially coaxial with axis A. It has been found that the displacement or offset distance C allows the catcher tube 94 time for movement to be kept small because the distance to be moved is decreased. Thus, the response time of the sorter 93 is reduced and the rapid segration of particles as illustrated in FIG. 5 is enhanced.

A flexible exit hose 105 is attached about the upper end 97 of the catcher tube 94 for transporting ensheathing fluid and the particles 68 sorted by the movement of the catcher tube 94. The tube 105 carries this dilute particle suspension of sorted particles 68 to a collection system 106. The collection system 106 includes a filter 107 used to collect sorted particles. The filter 107 is subject to a source of vacuum 108 which removes liquid from the particle suspension leaving just the particles on the filter 107. The source of vacuum 108 includes a safety filter 109 to prevent the escape of any aerosols from flask 111 and also prevents liquid from entering the vacuum system 108. A normally open pinch valve 110 may be used to selectively close flexible exit tube 105. A flask 111 is used as a trap to collect the liquid. Alternatively, the dilute suspension of sorted particles may be collected in a vessel by placing the end of hose 105 in the vessel for subsequent concentration by centrifugation or for use directly for culturing or analysis. The catcher tube sorter 93 is easy to use. There are no adjustments to make. The particles are collected on a filter ready to culture or examine microscopically. The sorting with a catcher tube does not disturb the analysis with pressure disturbances and does not contaminate the two fractions of flow (collected and not collected) with gas. There is a need to properly time the catcher tube motions; the transit time required for the particle to move from its analysis portion to the location where it first enters the catcher tube is about 600 microseconds. To accommodate variations in this transit time and to allow for the time required to move the catcher tube from one position to the other the driver 98 is energized earlier (at about 500 microseconds) and de-energized later (at about 700 microseconds). That additional time insures that the particle is well within the catcher tube, i.e. captured. Other signals could be used to automatically compensate for variations in transit time. Besides laser beam transit time, flow cell pressure drop, sheath flow rate, impact pressure on the catcher tube, sheath fluid temperature and the like or any combination thereof could be used.

A method for selectively sorting particles passing through the apparatus 10 is another form of the invention. The method includes generating a signal representative of one or more characteristics of the particles 68 passing through an analysis orifice 36 of the apparatus 10 and applying the signal to the driver 98 for changing the position of the catcher tube 94 so that the catcher tube 94 is moved to receive and sort characteristics.

The step of applying the signal to the driver 98 for changing the position of the catcher tube 94 may include flexing resilient support 101 for the catcher tube 94 to bring the axis B of the catcher tube 94 into substantial alignment with the particles exiting orifice 36. The step of generating the signal representative of one or more characteristics of the particles exiting through orifice 36 includes using light from laser 16 to analyze the particles passing one at a time through the flow cell orifice 36 to provide an electrical signal. The step of providing the electrical signal includes the step of applying the signal to the driver 98 for changing the position of the catcher tube 94 by flexing the resilient support 101 to align the catcher tube with the particles by pivoting the catcher tube 94 about the point 95 between its lower and upper ends 96 and 97.

The key advantages in the method and apparatus for sorting particles by moving catcher tube are that biohazardous aerosols or splashing are eliminated and no operator adjustments are required to set alignment of parts or electronic timing since all are set at time of manufacture. Similarly, no high voltage charging deflection system is necessary and no microscope droplet break off measuring or timing system adjustment is required. Therefore, the apparatus is low cost to manufacture. The overall system 93 provides a simple way of adding sorting capabilities to a particle analyzer.

While not shown it is within the present invention to realign the catcher tube 94 in ways other than pivotally such as by sliding to shift the axis B so as to be nearly coaxial with axis A. The support for the tube would have to be suitably modified to permit the requisite motion. Similarly sorted particles could also be collected in lumen 54. Skilled artisans will appreciate that many changes and refinements can be made to the design without deviating from the overall concept. The basic apparatus to which the catcher tube sorter 93 is applied may take many forms. The catcher tube sorter 93 can be used after any other form or analyzer, counter etc., such as (by way of example and not limitation) a volume (impedance) orifice.

What is claimed is:

1. A catcher tube sorter for a flow cytometer comprising:
   a body member having a passageway therethrough for the passage of particles which are to be analyzed, the passageway including an analysis portion, a pre-analysis portion and a post analysis portion;
   an uptake tube connected in fluid communication with the pre-analysis portion of the passageway and adapted for fluid communication with a source of particles for providing a particle flow path from the source of particles into the analysis portion;
   a catcher tube carried on the body member and mounted to be selectively positionable in fluid communication with the analysis portion for intermittently receiving analyzed particles after passage of particles through the analysis portion; and
   an operator connected to receive an input signal from the analysis portion relative to one or more particle characteristics and to activate the catcher tube for selectively positioning the catcher tube in fluid communication with the analysis portion.

2. The sorter of claim 1 wherein the analysis portion of the passageway includes a flowcell having an orifice sized to permit the passage of substantially one particle at a time through the analysis portion, and wherein the input signal is an optical response to one or more particle characteristics.

3. The sorter of claim 2 wherein the body member includes means for permitting light to be directed at the orifice at an angle substantially orthogonal to the direction of particle flow through the flowcell.

4. The sorter of claim 3 wherein the means for permitting light includes a recess for positioning a lens adjacent the flowcell.

5. The sorter of claim 2 wherein the operator means produces an electrical pulse of strength and duration sufficient to selectively position the catcher tube in fluid communication with the analysis portion.

6. The sorter of claim 5 wherein a driver mounted to the body member and associated with the catcher tube receives the input signal pulse and selectively positions the catcher tube in at least partial alignment for fluid communication with the analysis portion.

7. The sorter of claim 6 wherein the catcher tube has an axis and is carried on the body member for movement relative to the axis into partial alignment with the analysis portion.

8. The sorter of claim 7 wherein a sheathing liquid is introduced into the pre-analysis portion about an inner end of the uptake tube to provide a sheathed flow of particles along an axis of the passageway toward the analysis portion and the post analysis portion is arranged about the catcher tube to receive and direct away particle flow not selectively caught in the catcher tube.

9. A particle flow through apparatus comprising:
a body member having a passageway therethrough including an analysis region through which substantially one particle at a time may pass in the direction of flow through the analysis region when the apparatus is operating;
a sheathing liquid applied to the supply of particles in the passageway for hydrodynamic focusing the particles relative to the liquid;
catcher tube means supported upon the body member and associated with liquid and particles from the analysis region, the catcher tube positionable in a position substantially in alignment with the particles flowing from the analysis region for culling particles from the analysis region to another position where the catcher tube is not aligned with the particles flowing from the analysis region but is aligned with the fluid flowing from the analysis region; and
control means operatively responsive to particles of one or more preselected types passing through the analysis region, the control means arranged for moving the catcher tube between the positions substantially out of and into alignment with the flowing particles from the analysis region.

10. The apparatus of claim 9 wherein the catcher tube means includes a resilient support which is stressed upon movement of the catcher tube between the positions.

11. The apparatus of claim 10 wherein the control means includes a means responsive to at least one characteristic of one or more particles passing through the analysis region and a driver activated by the means responsive and connected to the catcher tube means for flexing the resilient support from the unaligned position to the aligned position.

12. A catcher tube sorter for a flow cytometer comprising:
a body member having a passageway therethrough for the passage of particles which are to be analyzed, the passageway including an analysis portion, a pre-analysis portion and post-analysis portion, all of which lie substantially on the same axis through the body member;
an uptake tube having an inner end positioned in the pre-analysis portion of the passageway adjacent the analysis portion and outer end extending outwardly of the body member for insertion into a pressurized sample supply containing liquid and particles, the uptake tube having a lumen extending therethrough for the passage of the particles toward the analysis portion of the passageway;
a flowcell included in the analysis portion and having an orifice sized to permit the passage of substantially one particle at a time through the analysis portion;
a catcher tube movable into fluid communication with the axis extending through the pre-analysis portion, analysis portion and the post-analysis portion; and
regulating means on the body member and operatively associated with the catcher tube for substantially aligning the catcher tube with the axis.

13. The sorter of claim 12 wherein the catcher tube is elongate with an axis and a flexible support moveably attaches the catcher tube to the body member for carrying the catcher tube in a position for realignment of the catcher tube axis with the passageway axis so that the axes are substantially coaxial with one another.

14. The sorter of claim 13 wherein the catcher tube includes a pair of ends and a central section therebetween and the flexible support attaches the central section of the catcher tube to the body member permitting pivotal movement about a point located along the catcher tube axis into the position for realignment of the catcher tube axis with the passageway axis so that the axes are displaced relative to one another.

15. The sorter of claim 14 wherein the catcher tube includes a driver located between an end of the catcher tube and the body member for moving an opposite end on the catcher tube into displaced alignment with the passageway axis.

16. A flow cytometer for determining one or more characteristics of particles or the like flowing in a liquid stream comprising:
means for moving particles in a liquid flow stream;
a body member having a passageway therethrough including an analysis region through which the moving particles pass substantially one at a time in the direction of flow;
a catcher tube sorting means having an elongate catcher tube operative to selectively receive flow from the passageway when the elongate catcher tube is longitudinal aligned with the passageway;
means for providing a beam of light to illuminate the particles passing through the analysis region;
means for detecting light with respect to each moving particle and for associating the detected light with one or more characteristics of each particle and to generate a signal responsive to the particle characteristics; and
means for receiving the signal and in response thereto to operatively position the elongate catcher tube in alignment with the passageway.

17. A method for sorting particles passing through a particle analysis apparatus for transporting a sample of particles carried in a liquid including the following steps;
generating a signal representative of one or more characteristics of the particles passing through an analysis region of the analysis apparatus,
applying the signal to a driver for changing the position of a catcher tube so that the catcher tube is moved to receive the particles having one or more of the characteristics.

18. The method of claim 17 wherein the step of applying the signal to a driver for changing the position of the catcher tube includes flexing a support for the catcher tube to bring the catcher tube into substantial alignment with the particles passing through the particle analysis apparatus and having one or more of the characteristics.

19. The method of claim 17 wherein the step of generating a signal representative of one or more characteristics of the particles passing through an analysis region includes using light to analyze the particles passing one at a time through the analysis region and to provide an electrical signal.

20. The method of claim 19 wherein the step of using light to analyze the particles passing one at a time through the analysis region and to provide an electrical signal includes as a step thereof applying the signal to a driver for changing the position of a catcher tube.

21. The method of claim 18 wherein the step of positioning the catcher tube to bring the catcher tube into substantial alignment with the particles includes as a step thereof pivoting the catcher tube about a point located between the ends of the catcher tube.

22. The sorter of claim 15 wherein said driver is a piezo electric device responsive to voltage.

23. A catcher tube sorter for a flow cytometer comprising:
- a body member haivng a passageway therethrough for the passage of particles which are to be analyzed, the passageway including an analysis portion, a pre-analysis portion and post-analysis portion, all of which lie substantially on the same axis through the body member;
- an uptake tube having an inner end positioned in the pre-analysis portion of the passageway adjacent the analysis portion and outer end extending outwardly of the body member for insertion into a sample supply containing liquid and particles, the uptake tube having a lumen extending therethrough for the passage of the particles toward the analysis portion of the passageway;
- a flowcell included in the analysis portion and having an orifice sized to permit the passage of substantially one particle at a time through the analysis portion;
- a catcher tube movable into fluid communication with the axis extending through the pre-analysis portion, analysis portion and the post-analysis portion; and
- regulating means on the body member and operatively associated with the catcher tube for substantially aligning the catcher tube with the axis.

24. The sorter of claim 23 wherein the catcher tube is elongate with an axis and a flexible support moveably attaches the catcher tube to the body member for carrying the catcher tube in a position for realignment of the catcher tube axis with the passageway axis so that the axes are substantially coaxial with one another.

25. The sorter of claim 24 wherein the catcher tube includes a pair of ends and a central section therebetween and the flexible support attaches the central section of the catcher tube to the body member permitting pivotal movement about a point located along the catcher tube axis into the position for realignment of the catcher tube axis with the passageway axis so that the axes are displaced relative to one another.

26. The sorter of claim 25 wherein the catcher tube includes a driver located between an end of the catcher tube and the body member for moving an opposite end on the catcher tube into displaced alignment with the passageway axis.

27. The sorter of claim 26 wherein said driver is a piezo electric device responsive to voltage.

* * * * *